United States Patent [19]

Han

[11] Patent Number: 5,155,367
[45] Date of Patent: Oct. 13, 1992

[54] GAS CONTAMINATION-MEASURING APPARATUS FOR USE WITH AN ULTRAVIOLET-EMITTING LASER SOURCE

[75] Inventor: Woo-Sung Han, Suweon, Rep. of Korea

[73] Assignee: Samsung Electronics Co., Ltd., Suweon, Rep. of Korea

[21] Appl. No.: 617,812

[22] Filed: Nov. 26, 1990

[30] Foreign Application Priority Data

Oct. 10, 1990 [KR] Rep. of Korea .............. 90-16055[U]

[51] Int. Cl.⁵ .................... G01N 21/17; G01N 21/27; G01N 21/47
[52] U.S. Cl. .................... 250/372; 250/215; 356/445; 356/448
[58] Field of Search ............... 250/372, 373, 215, 574, 250/573, 526; 372/57, 59; 356/445, 448, 446

[56] References Cited

U.S. PATENT DOCUMENTS

| | | | |
|---|---|---|---|
| 4,284,356 | 8/1981 | Heilman | 356/446 |
| 4,302,206 | 11/1981 | Profeta et al. | 250/373 |
| 4,365,896 | 12/1982 | Mihalow | 356/446 |
| 4,538,064 | 8/1985 | Kovacs | 250/231.1 |
| 4,779,988 | 10/1988 | Horiguichi | 356/445 |
| 4,814,628 | 3/1989 | Eichweber | 250/574 |
| 4,965,454 | 10/1990 | Yamauchi et al. | 250/372 |

Primary Examiner—Constantine Hannaher
Assistant Examiner—Edward J. Glick
Attorney, Agent, or Firm—Cushman, Darby & Cushman

[57] ABSTRACT

A gas contamination measuring apparatus is equipped at the front side of the light path for detecting whether environmental contamination is present. The gas contamination measuring apparatus includes a nitrogen injecting inlet, a nitrogen exiting outlet, the quartz plate, an inside contamination detecting light emitting element and a photoreceiving element detecting light emitting element and a photoreceiving element and an outside contamination detecting light emitting element and a photoreceiving element.

7 Claims, 5 Drawing Sheets

GAS CONTAMINATION-MEASURING APPARATUS FOR USE WITH AN ULTRAVIOLET-EMITTING LASER SOURCE

BACKGROUND OF THE INVENTION

1. Field of the Invention

The present invention relates to a gas contamination measuring apparatus, more particularly, to an apparatus which is installed at the front side of the light path of an ultravioletemitting laser apparatus to detect the presence of environmental contamination.

2. Description of the Related Art

Recently, the group of high output lasers (excimer lasers) has been used in generating light in the UV range of the spectrum (for example, XeF laser at 353 nm, XeCl laser at 308 nm, KrF laser at 248 nm, ArF laser at 193 nm, $F_2$ laser at 157 nm, $XeB_2$, etc.).

The lasers are stimulated or pumped by the action of discharge, excitation by collision of electrons, or vibration of a resonator.

These lasers, however, may be used as simply movable wave amplifiers without a resonator. If an ultrashort pulse of light having a wavelength within the amplification range of the excimer laser used is provided and its action condition is set properly, it is possible to obtain an ultrashort pulse with very high sensitivity.

Conventionally, the laser beam produced from laser apparatus which generates ultraviolet rays or deep ultraviolet rays has powerful energy of which the mean power is several hundred thousand watts and the peak power produced is up to $10^5 \sim 10^{10}$ watts. Accordingly, if dirt is present in the laser path, the dirt is resolved and changed into reaction products which are deposited onto the optical elements, thereby resulting in problems that the strength of laser is decreased and the functional element in the laser apparatus must be changed.

SUMMARY OF THE INVENTION

Accordingly, an object of the present invention is to solve the problems of the prior art and to provide a gas contamination measuring apparatus in which a contamination detecting element attaches onto the inner and outer sides of the gas contamination measuring apparatus and gathers and analyzes the material depositing on the inner and outer sides of the quartz plate in order to detect the progressing rate and the degree of the contamination.

Another object of the present invention is to extend the life of a laser apparatus, by checking the environment where optical devices of the laser apparatus are placed.

DETAILED DESCRIPTION OF THE INVENTION

Thereafter, the present invention will be described in detail with reference to the accompanying drawings.

Figure 1A:
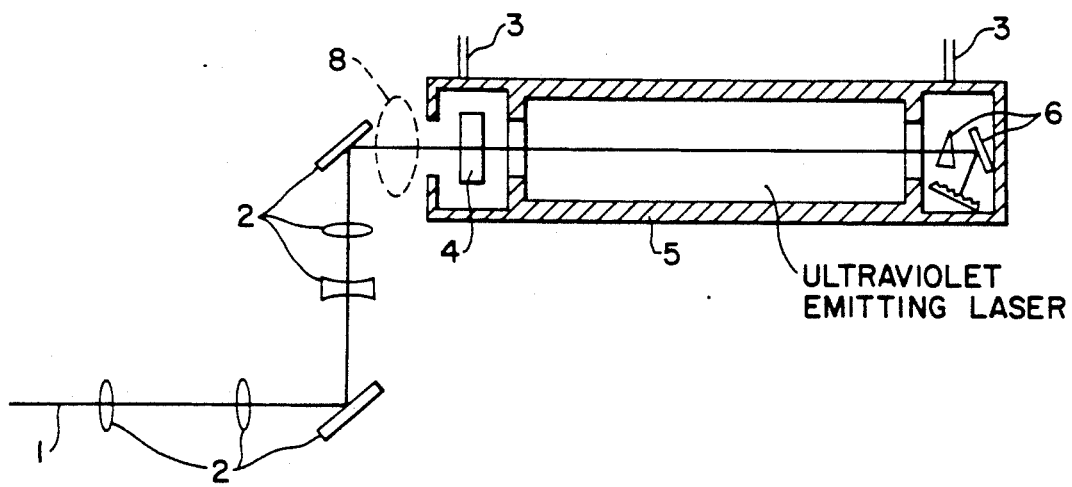
FIG. 1A is a general diagrammatic view of a conventional laser generating apparatus provided with the gas contamination measuring apparatus of the present invention.

FIG. 1A shows a general diagrammatic view showing otherwise conventional ultraviolet-emitting laser generating apparatus 5 and also shows the preferred location, at 8, of the gas contamination measuring apparatus of the present invention. As indicated above, the conventional laser apparatus may be a high output laser (i.e., an excimer laser) which generates light in the UV range of the spectrum, for example, an XeF laser at 353 nm, an XeCl laser at 308 nm, a KrF laser at 248 nm, an ArF laser at 193 nm or an $F_2$ laser at 157 nm. In the foregoing examples, "XeF", etc., designates the working gas of the laser. For the laser light beam ! generated from the laser generating apparatus, the required wavelength is filtered by the wavelength filtering device 6. It is then determined whether the filtered light beam has the correct wavelength, and, if it does, then light 1 is output and transmitted to the destination via the optical elements 2. In FIG. 1A, reference numeral 8 shows a preliminary position where the gas contamination measuring apparatus is to be installed, according to the present invention.

In using the apparatus, nitrogen is injected through the nitrogen injecting inlet 3 to the chambers of the laser apparatus which respectively house wavelength measuring element 4 and the wavelength filtering element 6, to remove the air from the vicinity of those elements thereby preventing strongly oxidizing ozone $O_3$ from being produced in those chambers by the interaction of the laser beam with oxygen.

Alternatively, when nitrogen, for manufacturing or in use, is subjected to cross-contamination through the other equipment, the contamination materials (e.g., a hydrocarbon compound, that is, an organic matter, and/or inorganic mater such as sulphur, oxygen, silicon and the like) can be undesirably resolved by the laser beam in the chambers housing elements 4 and 6, and, as a result, undesirably deposited onto the wavelength measuring element 4 and the wavelength filtering element 6, so that the output of laser is reduced, the central wavelength of laser is varied up to several tens per million and also the bandwidth of laser is expanded to several tens per million. Therefore, it is impossible to use the laser light beam as the light source in the photo processing of semiconductor parts.

Furthermore, in the optical elements 2, inorganic matter and organic matter, such as oxygen or the like, in the atmosphere are resolved by the laser and the reactants are deposited thereon, so the strength of the light from the used end of the laser is reduced and the efficiency of the light is decreased.

Figure 1B:
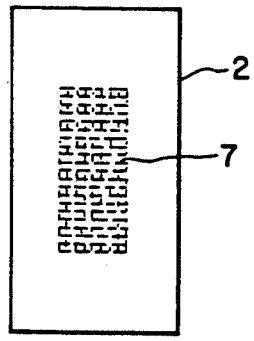
FIG. 1B is a diagrammatic view showing an optical element of the laser beam-generating apparatus of FIG. 1A, as contaminated by a source of contamination.

FIG. 1B shows a portion of the optical element contaminated by means of the contamination source.

Figure 2A:
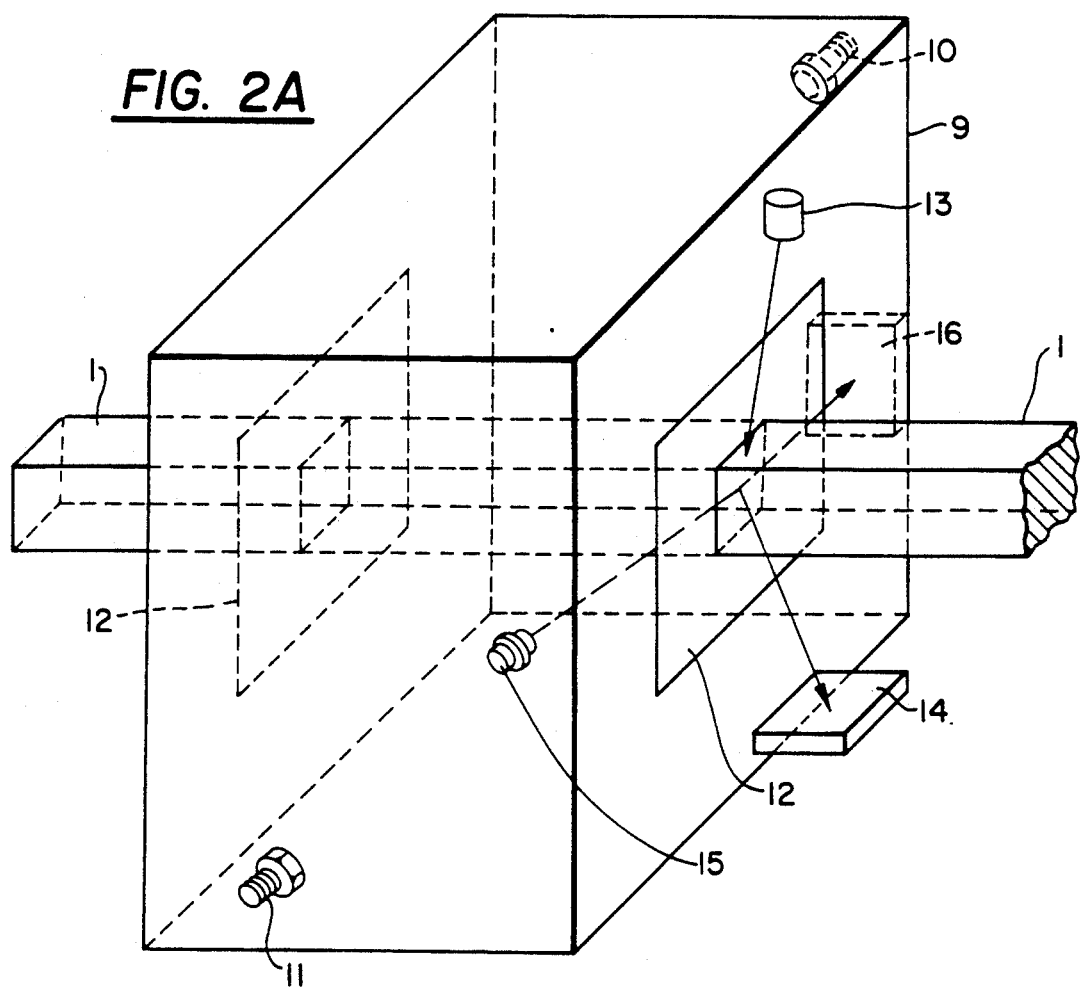
FIG. 2A is a perspective view of a gas contamination measuring apparatus according to the present invention.

FIG. 2A is a perspective view showing the contamination detecting apparatus according to the present invention.

In use of the gas contamination measuring apparatus 9 of the present invention, as shown in FIG. 2A, nitrogen which is slated for used as a gas to purge air from the chambers housing the elements 4 and 6 of the laser apparatus 5, is injected into the inner part of the apparatus 9 through the nitrogen injecting inlet 10 and the apparatus is placed at the same space as that of the optical element 2 shown in FIG. 1 so that the contaminating material in the atmosphere around the optical element 2 is deposited in the outer side of the quartz plate 12 of the apparatus 9, to collect and the deposited material for analysis. Then, the optical element 2 is moved to a different environment to ensure the progressing rate and the degree o contamination thereon.

Furthermore, the inside contamination detecting light emitting photoreceiving elements 15 and 16, and the outside contamination detecting light emitting photoreceiving elements 13 and 14 are provided in order to permit the detection of inside and outside contaminations.

On FIG. 2A, reference numeral 11 shows a nitrogen exiting outlet from the chamber of the apparatus 9.

Figure 2B:
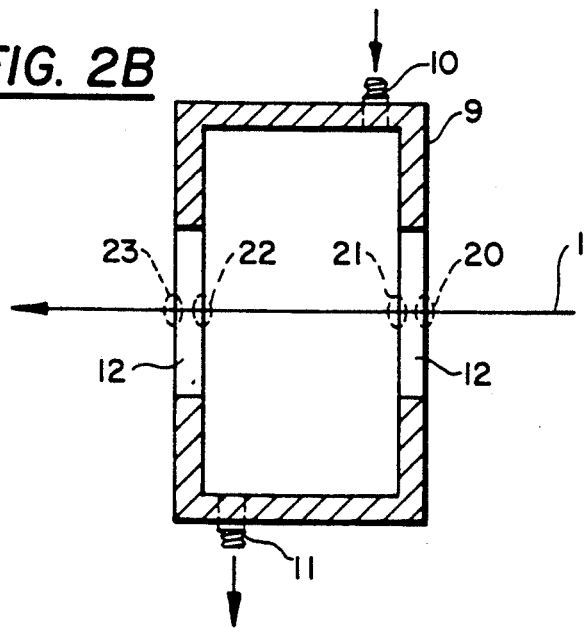
FIG. 2B is a horizontal longitudinal cross-sectional diagram of a gas contamination measuring apparatus according to the present invention.

FIG. 2B is a cross-sectional diagram, of the contamination detecting apparatus 9 according to the present invention, viewed from above. In this drawing is shown the surfaces 20, 21, 22, and 23 onto which can be deposited contamination material from nitrogen atmosphere and impurities in the atmosphere which surround the apparatus 9 while the laser light 1 passes through the quartz plate 12.

Figure 3A:
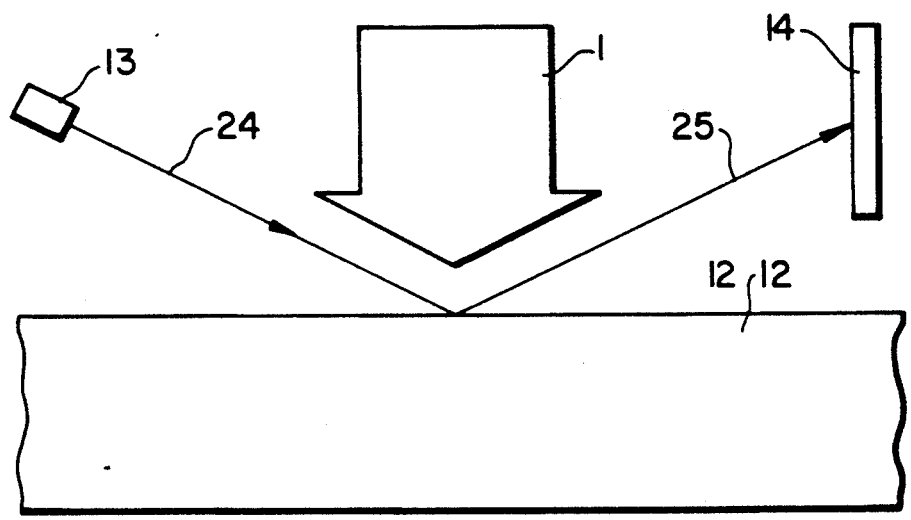
FIG. 3A is a diagrammatic view showing a non-contaminated quartz plate.

FIG. 3A is a view showing the non-contamination state of the quartz plate 12 and the drawing shows the detecting process of the reflected light, from the incident detecting light 24, using the photoreceiving element 14.

Figure 3B:
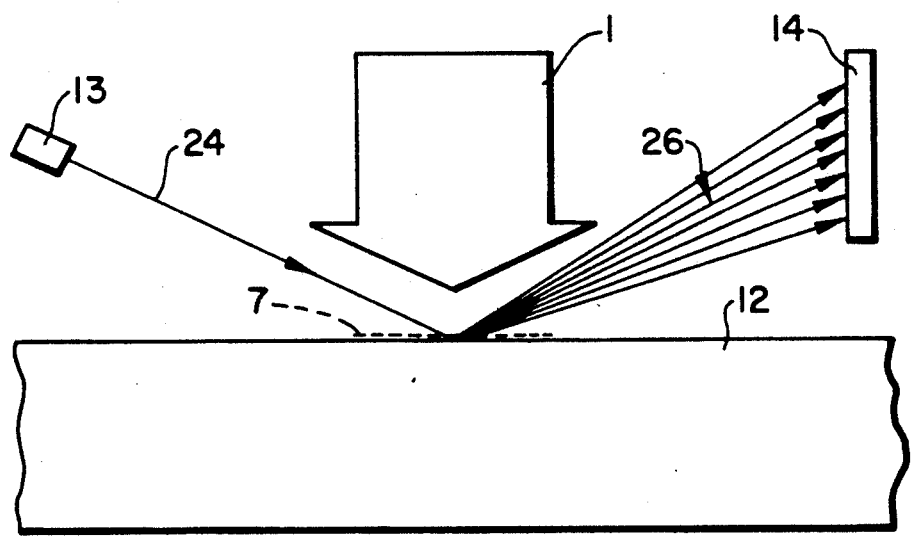
FIG. 3B is a view showing a detecting process for an incident light dispersed by means of the photoreceiving element.

Meanwhile, FIG. 3B shows a process for detecting the dispersed light in the incident detecting light 24 and in FIG. 3B reference numeral 7 shows a contaminated portion of the optical element.

Figure 3C:
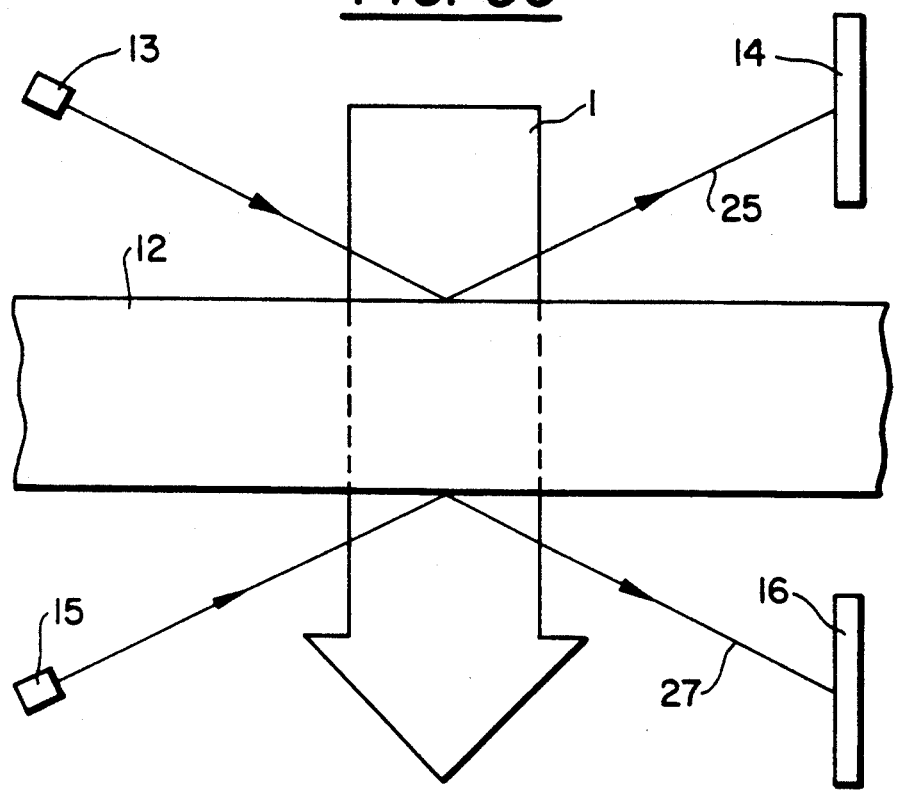
FIG. 3C is a view showing the incidence of the detected light on the inner and outer sides of the quartz plate.

Also, FIG. 3C is a view showing the incidence of the detected light on the inner and outer sides of the quartz plate 12 and shows the detecting process of the detected light reflecting from the quartz plate 12 by the contaminated detecting photoreceiving elements 14 and 16. At this time, for the light emitting elements 13 and 15, there may be used a collimated lamp or a light source such as an HeNe laser, or an LED. Linear array-type CCD diodes or photo diodes may be used as the inner and outer contamination detecting photoreceiving elements 14 and 16.

Figure 4:
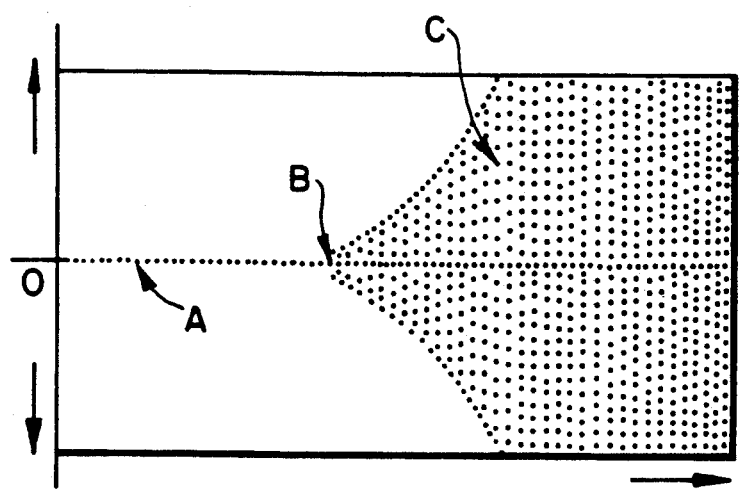
FIG. 4 is a view showing the occupied area of the photoreceiving element with time variation; and, FIG. 5 is a view illustrating the process for alternatively measuring contamination in the nitrogen gas from each of a plurality of alternately useful supply lines.

FIG. 4 is a diagrammatic view showing the occupied area of the photoreceiving element, with time-variation. At the beginning along the axis of the time, the light is incident on merely a small area, i.e., the front end of the photoreceiving element 14. This means that the quartz plate 12 is not contaminated and thus the light is not reflected (i.e., the portion indicated by A in the drawing). However, when a predetermined time has elapsed, the quartz plate 12 becomes opaquely contaminated. This is because the proportion of the light being dispersed is increased, until it fills up the entirety of the photoreceiving element 14. In this case, the contamination degree of the quartz plate 12 can be confirmed by using the AES of FTIR technique (see portion C in the drawing).

For example, when a KrF laser (248nm) is used at the range of $2 \times 10^8$ pulses, the intensity of the laser is reduced to 40 $\mu$J/pulse. cm$^2$ from 160 $\mu$J/pulse. cm$^2$. Since the apparatus of the present invention emits 200 pulses per second, the intensity of the laser is reduced to 40 $\mu$J/pulse. cm$^2$ depending upon a time indicated by the following equation:

$2 \times 10^8$ pulses/(200 pulse/sec $\times$ 60 sec/min) = 16666.7 min.

At this time, the amount of the hydrocarbon in the nitrogen, N$_2$ is 0.3 ppm. Furthermore, when N$_2$ flows at the rate of 10 l/min through the gas contamination measuring apparatus of the present invention, it more rapidly reaches the position B of FIG. 4, by $1.8 \times 10^7$ pulses, than the case of the same hydrocarbon content of 0.3 ppm. That is, the degree of the contamination appears in only 1500 min, obtained from the following equation:

$1.8 \times 10^7$ pulses/(200 pulses/sec $\times$ 60 sec/min) = 1500 min.

Meanwhile, when more carrier gas passes through the apparatus of the present invention, the time necessary for reaching the point B shown in FIG. 4 is shorter, so that the apparatus and method of the present invention can determine whether the quality of the carrier gas is excellent or not.

Figure 5:
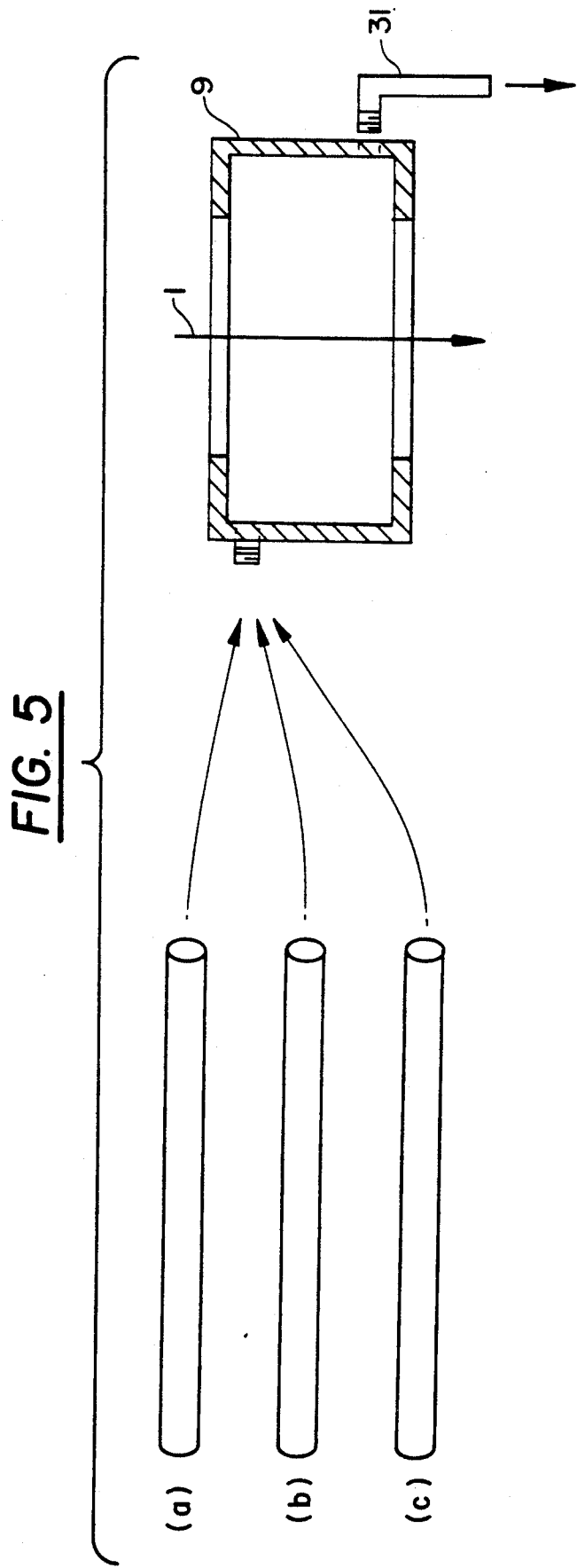

FIG. 5 is a view showing the process for measuring the degree of the contamination of a plurality of the nitrogen lines. In FIG. 5, reference numeral 31 shows the nitrogen exiting hose connected to the outlet II of t he chamber of the apparatus 9. In this process, each nitrogen line is connected to the nitrogen inlet 10 of the chamber of the gas contamination measuring apparatus, one line at a time, to measure the degree of the contamination of the nitrogen gas flowing therefrom. Also, the quartz plates 12 must be exchanged together each time the lines change and then the data obtained must be compared with data of FIG. 4.

In the compared result, when the state of the portion A shown in FIG. 4 is maintained for a long while, the line is determined to be an excellent one. Accordingly, the nitrogen may be selectively provided to the chamber of the laser apparatus 5 which respectively house wavelength measuring element 4 and the wavelength filtering element 6, and the resultant excellent nitrogen is selectively provided as a gas for purging, or for other uses in a process.

As mentioned above, the gas contamination measuring apparatus according to the present invention can detect the presence of the hydrocarbon compounds or the impurities, contained in nitrogen, such as sulphur, silicon, etc. In addition, the apparatus can check the environment in which there is being installed the optical elements which guide the path of light, in order that laser or excimer laser, which produce, respectively, ultraviolet rays and deep ultraviolet rays can be used in a process for manufacturing semiconductors, or for the purpose of a medical service. Accordingly, the manufacturing or medical apparatus may be used in a non-contaminated environment, whereby the life of the laser or excimer laser can be extended.

Furthermore, the purity of nitrogen can be previously ensured, so that the wavelength measuring element and the wavelength filtering element can be used for a longer time without cleaning or replacement in the laser or excimer laser apparatus.

Although the invention has been described with reference to the embodiments specifically illustrated above, many modifications and variations are possible within the scope of the invention.

What is claimed is:

1. A gas contamination measuring apparatus for a laser, comprising:

a laser device including means for generating and emitting a laser beam in the ultraviolet or deep ultraviolet range, along a path, and in which the generated laser beam, prior to being emitted from the device, is incident upon or passes through at least one element which is housed in means defining a chamber from which air is purged by a stream of nitrogen gas; said chamber defining means including a nitrogen gas inlet to and a nitrogen gas outlet from said chamber; and in which device the generated laser beam is incident upon or passes through at least one optical element which is exposed to air that is located further along said path from aid emitting means than said chamber;

a housing having a quartz plate inlet window and a quartz plate outlet window; said housing being disposed in said laser beam path so that said laser beam passes into said housing through said inlet window and passes out of said housing through said outlet window; means providing an inlet into and an outlet from said housing, of said stream of nitrogen gas;

a first pair of light-emitting and light-detecting elements, respectively arranged to direct a light beam onto a first inner surface of one of said quartz plate windows inside said housing and to detect light thereby reflected from that inner surface inside said housing, from a first site in said path, so that a change in detected light reflected from said first site on said first, inner surface can be used as a measure of contamination in said stream of nitrogen gas; and a second pair of light-emitting and light-detecting elements, respectively arranged to direct a light beam onto a second, outer surface of one of said quartz plate windows outside said housing and to detect light thereby reflected from that outer surface outside said housing, from a second site in said path, so that a change in detected light reflected from said second site on said second, outer surface can be used as a measure o contamination in said air.

2. The gas contamination measuring device of claim 1, wherein:

said means for generating and emitting a laser beam is a laser or excimer laser which uses a working gas selected from the group consisting of XeF, XeCl, KrF, KrCl and XeBz, and which respectively emits a laser light beam having a wave length of 351 nm, 308 nm, 248 nm, 222 nm and 282 nm.

3. The gas contamination measuring device of claim 1, wherein in each of said pairs of light-emitting and light-detecting elements, the light-detecting element is a linear array of CCD diodes.

4. The gas contamination measuring device of claim 1, wherein:

in each of said pairs of light-emitting and light-detecting elements, the light-detecting element is a linear array of photodiodes.

5. The gas contamination measuring device of claim 1, wherein:

in each of said pairs of light-emitting and light-detecting elements, the light-emitting element is a collimated lamp.

6. The gas contamination measuring device of claim 1, wherein:

in each of said pairs of light-emitting and light-detecting elements, the light-emitting element is an HeNe laser.

7. The gas contamination measuring device of claim 1, wherein:

in each of said pairs of light-emitting and light-detecting elements, the light-emitting element is at least one LED.

* * * * *